(12) United States Patent
Viswanathan

(10) Patent No.: US 7,751,867 B2
(45) Date of Patent: Jul. 6, 2010

(54) CONTACT OVER-TORQUE WITH THREE-DIMENSIONAL ANATOMICAL DATA

(75) Inventor: Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 1101 days.

(21) Appl. No.: 11/314,826

(22) Filed: Dec. 20, 2005

(65) Prior Publication Data

US 2007/0137656 A1     Jun. 21, 2007

Related U.S. Application Data

(60) Provisional application No. 60/637,504, filed on Dec. 20, 2004.

(51) Int. Cl.
A61B 5/05 (2006.01)
A61B 19/00 (2006.01)

(52) U.S. Cl. ............ 600/424; 600/407; 600/411; 128/899

(58) Field of Classification Search ............ None
See application file for complete search history.

(56) References Cited

U.S. PATENT DOCUMENTS

| | | | |
|---|---|---|---|
| 5,654,864 A | 8/1997 | Ritter et al. |
| 5,931,818 A | 8/1999 | Werp et al. |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |
| 6,157,853 A | 12/2000 | Blume et al. |
| 6,212,419 B1 | 4/2001 | Blume et al. |
| 6,241,671 B1 | 6/2001 | Ritter et al. |
| 6,292,678 B1 | 9/2001 | Hall et al. |
| 6,296,604 B1 | 10/2001 | Garibaldi et al. |
| 6,298,257 B1 | 10/2001 | Hall et al. |
| 6,304,768 B1 | 10/2001 | Blume et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |

(Continued)

OTHER PUBLICATIONS

International Search Report and Written Opinion Dated: Sep. 27, 2007 Pages: 7.

*Primary Examiner*—Long V Le
*Assistant Examiner*—Angela M Hoffa
(74) *Attorney, Agent, or Firm*—Harness, Dickey & Pierce, P.L.C.

(57) ABSTRACT

A method is provided for establishing contact of a medical device against a three-dimensional surface geometry within a subject body, the method comprising obtaining a three-dimensional tissue surface geometry of an anatomical region within the subject body, obtaining a target location on the surface for the device to contact, determining local surface geometry information in a neighborhood of the target location, and using this information to determine a change of at least one control variable for effecting an over-torque of the medical device to enhance contact of the device with the target surface.

2 Claims, 1 Drawing Sheet

U.S. PATENT DOCUMENTS

| | | | |
|---|---|---|---|
| 6,459,924 | B1 | 10/2002 | Creighton, IV et al. |
| 6,505,062 | B1 | 1/2003 | Ritter et al. |
| 6,507,751 | B2 | 1/2003 | Blume et al. |
| 6,522,909 | B1 | 2/2003 | Garibaldi et al. |
| 6,524,303 | B1 | 2/2003 | Garibaldi |
| 6,527,782 | B2 | 3/2003 | Hogg et al. |
| 6,537,196 | B1 | 3/2003 | Creighton, IV et al. |
| 6,542,766 | B2 | 4/2003 | Hall et al. |
| 6,562,019 | B1 | 5/2003 | Sell |
| 6,630,879 | B1 | 10/2003 | Creighton, IV et al. |
| 6,662,034 | B2 | 12/2003 | Segner et al. |
| 6,677,752 | B1 | 1/2004 | Creighton, IV et al. |
| 6,702,804 | B1 | 3/2004 | Ritter et al. |
| 6,733,511 | B2 | 5/2004 | Hall et al. |
| 6,755,816 | B2 | 6/2004 | Ritter et al. |
| 6,817,364 | B2 | 11/2004 | Garibaldi et al. |
| 6,834,201 | B2 | 12/2004 | Gillies et al. |
| 6,902,528 | B1 | 6/2005 | Garibaldi et al. |
| 6,911,026 | B1 | 6/2005 | Hall et al. |
| 6,968,846 | B2 | 11/2005 | Viswanathan |
| 6,975,197 | B2 | 12/2005 | Creighton, IV |
| 6,980,843 | B2 | 12/2005 | Eng et al. |
| 7,008,418 | B2 | 3/2006 | Hall et al. |
| 7,010,338 | B2 | 3/2006 | Ritter et al. |
| 7,019,610 | B2 | 3/2006 | Creighton, IV et al. |
| 7,020,512 | B2 | 3/2006 | Ritter et al. |
| 7,066,924 | B1 | 6/2006 | Garibaldi et al. |
| 7,072,703 | B2 | 7/2006 | Zhang et al. |
| 2001/0038683 | A1 | 11/2001 | Ritter et al. |
| 2002/0019644 | A1 | 2/2002 | Hastings et al. |
| 2002/0177789 | A1 | 11/2002 | Ferry et al. |
| 2004/0006301 | A1 | 1/2004 | Sell et al. |
| 2004/0019447 | A1 | 1/2004 | Shachar |
| 2004/0064153 | A1 | 4/2004 | Creighton, IV et al. |
| 2004/0068173 | A1 | 4/2004 | Viswanathan |
| 2004/0096511 | A1 | 5/2004 | Harburn et al. |
| 2004/0133130 | A1 | 7/2004 | Ferry et al. |
| 2004/0157082 | A1 | 8/2004 | Ritter et al. |
| 2004/0158972 | A1 | 8/2004 | Creighton, IV et al. |
| 2004/0186376 | A1 | 9/2004 | Hogg et al. |
| 2004/0199074 | A1 | 10/2004 | Ritter et al. |
| 2004/0249262 | A1 | 12/2004 | Werp et al. |
| 2004/0249263 | A1 | 12/2004 | Creighton, IV |
| 2004/0260172 | A1 | 12/2004 | Ritter et al. |
| 2005/0020911 | A1 | 1/2005 | Viswanathan et al. |
| 2005/0043611 | A1 | 2/2005 | Sabo et al. |
| 2005/0065435 | A1 | 3/2005 | Rauch et al. |
| 2005/0096589 | A1 | 5/2005 | Shachar |
| 2005/0113628 | A1 | 5/2005 | Creighton, IV et al. |
| 2005/0113812 | A1 | 5/2005 | Viswanathan et al. |
| 2005/0119687 | A1 | 6/2005 | Dacey, Jr. et al. |
| 2005/0182315 | A1 | 8/2005 | Ritter et al. |
| 2005/0256398 | A1 | 11/2005 | Hastings et al. |
| 2006/0009735 | A1 | 1/2006 | Viswanathan et al. |
| 2006/0025679 | A1 | 2/2006 | Viswanathan et al. |
| 2006/0036125 | A1 | 2/2006 | Viswanathan et al. |
| 2006/0036163 | A1 | 2/2006 | Viswanathan |
| 2006/0041178 | A1 | 2/2006 | Viswanathan et al. |
| 2006/0041179 | A1 | 2/2006 | Viswanathan et al. |
| 2006/0041180 | A1 | 2/2006 | Viswanathan et al. |
| 2006/0041181 | A1 | 2/2006 | Viswanathan et al. |
| 2006/0041245 | A1 | 2/2006 | Ferry et al. |
| 2006/0058646 | A1 | 3/2006 | Viswanathan |
| 2006/0074297 | A1 | 4/2006 | Viswanathan |
| 2006/0079745 | A1 | 4/2006 | Viswanathan |
| 2006/0079812 | A1 | 4/2006 | Viswanathan |
| 2006/0093193 | A1 | 5/2006 | Viswanathan |
| 2006/0094956 | A1 | 5/2006 | Viswanathan |
| 2006/0100505 | A1 | 5/2006 | Viswanathan |
| 2006/0114088 | A1 | 6/2006 | Shachar |
| 2006/0116633 | A1 | 6/2006 | Shachar |
| 2006/0144407 | A1 | 7/2006 | Aliberto et al. |
| 2006/0144408 | A1 | 7/2006 | Ferry |

CONTACT OVER-TORQUE WITH THREE-DIMENSIONAL ANATOMICAL DATA

CROSS-REFERENCE TO RELATED APPLICATIONS

This application claims the benefit of U.S. provisional patent application Ser. No. 60/637,504, filed Dec. 20, 2004, the entire disclosure of which is incorporated herein by reference.

FIELD OF THE INVENTION

This invention relates to control of medical devices in a subject body, and more particularly to placement of medical devices in a target location of the subject body.

BACKGROUND OF THE INVENTION

Interventional medicine is the collection of medical procedures in which access to the site of treatment is made through one of the patient's blood vessels, body cavities or lumens. For example, electro-physiology mapping of the heart is most often performed using a catheter which may be inserted into a patient's arterial system through a puncture of the femoral artery in the groin area. Other interventional medical procedures include assessment and treatment of tissues on the inner surfaces of the heart (endocardial surfaces) accessed via peripheral veins or arteries, treatment of vascular defects such as cerebral aneurysms, removal of embolic clots and debris from vessels, treatment of tumors via vascular access, endoscopy of the intestinal tract, etc.

Interventional medicine technologies have been applied to manipulation of instruments which contact tissues during surgical procedures, making these procedures more precise, repeatable and less dependent of the device manipulation skills of the physician. Some presently available interventional medical systems for directing and manipulating the distal tip of a medical device by actuation of the distal portion of the device use computer assisted navigation and an imaging system for providing imaging of the device and blood vessels and tissues. Such systems can control the navigation of a medical device, such as a catheter, to a target destination in an operating region using a computer to orient and guide the distal tip through blood vessels and tissue. In some cases, when the computed direction for reaching the target destination is determined and the medical device is extended, it is desired to establish sufficient contact of the medical device with the intended target location on the three dimensional tissue surface. Adequate contact with the tissue surface within the subject body is important, for instance, in the analysis and treatment of cardiac arrhythmias. A method is therefore desired for controlling movement of a medical device that will establish adequate contact with the target tissue surface and will allow for treatment of the targeted area.

SUMMARY OF THE INVENTION

The method and apparatus of the present invention facilitates the placement of the distal end of a medical device, such as a catheter or microcatheter, against a target location on a three-dimensional curved surface within a subject body. Generally, the present invention comprises a method for establishing contact of a medical device against a three-dimensional surface geometry within a subject body, the method comprising obtaining a three-dimensional tissue surface geometry of a location within the subject body, identifying a desired target location on the surface, computationally determining at least one point spaced from the desired target, stepping a minimum distance from the at least one point to determine whether an image threshold is crossed, and determining a change of at least one control variable for effecting an over-torque of a medical device to enhance contact of the device with the target surface.

In one aspect of the present invention, a three-dimensional surface geometry is suitably rendered in an image model and registered with a known location within the subject body. The model may be used to perform a stepping process to determine if an image surface threshold is crossed, and to determine at least one control variable that may be changed to effect a movement of a virtual or real medical device. The image model of the three-dimensional surface geometry and medical device may be used to predict over-torque of the real or virtual medical device corresponding to the control variable.

In another aspect of the present invention, at least some embodiments of a method provide for determining an over-torque magnetic field to be applied to a medical device to establish adequate contact of the medical device against the target surface of the subject body. In one embodiment, the method allows the user to identify the desired location on an image of the body, which is used to determine an appropriate over-torque rotation corresponding to the local surface geometry at the target location. These and other features and advantages will be in part apparent, and in part pointed out hereinafter.

DETAILED DESCRIPTION OF THE INVENTION

Figure 1:
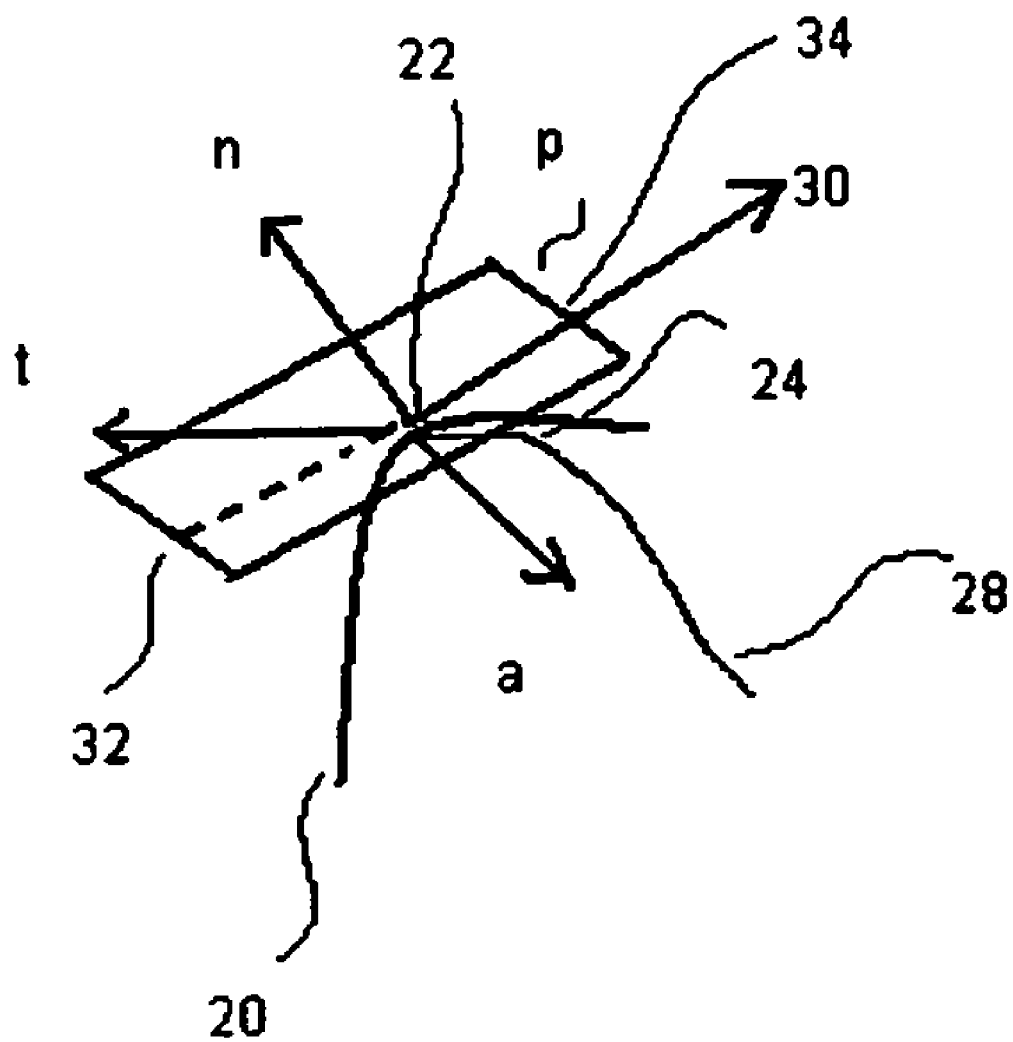
FIG. 1 is an illustration of a curved three dimensional tissue surface and a medical device held in contact with the surface through the over-torque method in accordance with the principles of the present invention.

In a preferred embodiment of the present invention, a method for establishing contact over-torque of the tip of a medical device against a tissue surface within a subject body is provided in accordance with the principles of the present invention. In one embodiment, the method provides for enhancing contact of a medical device with a tissue surface such as the heart, through the suitable application of an over-torque magnetic field. While this embodiment is operable with magnetically navigable medical devices, other embodiments of a method in accordance with the present invention may be used with medical devices that are guided without magnetic navigation but instead use other control methods for remote navigation such as mechanical actuation, electrostrictive actuation, or hydraulic actuation. The method for establishing contact of a medical device against a surface within a subject body comprises obtaining a three-dimensional tissue surface geometry of a region within the subject body, identifying a desired target location on the surface, defining at least one point spaced from the desired target, computationally stepping a minimum distance from the at least one point to determine whether an image threshold is crossed, and determining a change of at least one control variable for effecting an over-torque of a medical device to enhance contact of the device with the target surface.

A medical device such as a catheter may be navigated to the interior of a subject body of a patient by various means, including but not limited to magnetic navigation. Once the medical device has been navigated to a target surface of the body, such as a heart wall, the contact of the medical device against the tissue may be enhanced by suitably over-torquing the medical device against the tissue surface. A virtual representation of the medical device may be suitably rendered in a three-dimensional model of the surface geometry, and the method may then be used to determine a change to a control variable for affecting an over-torque of the medical device against the surface tissue. Such virtual modeling of the medical device may be used to predict the over-torque of the medical device prior to movement of the actual medical device. Where the medical device is a magnetically navigable medical device, the over-torque may be applied through the application of a magnetic field. Where a magnetically navigable medical device is used, for example, this may be accomplished by applying a magnetic moment in a direction that provides the maximum over torque (i.e., leads the orientation of the catheter tip by an angle of approximately 90° as measured about an axis that is normal to the plane defined by the catheter tip orientation and the local surface normal). This over-torque may be used to enhance contact with the tissue to obtain improved electro-physiology electrical readings, or to apply improved ablation treatment. A suitable over-torque of the magnetic field and the medical device depends on the local surface geometry of the target location within the body. In the following we shall describe the particular case when magnetic field actuation is used to remotely navigate the medical device, as a non-limiting example of an actuation method. Other actuation techniques could be employed as would be familiar to persons skilled in the art of remote surgical navigation.

Referring to FIG. 1, the tissue surface 20 of a three dimensional object in a subject body is represented by curve having a tangential plane p and an outward unit normal vector $\bar{n}$ at a target location point $\bar{x}_0$ (indicated at 22). The local surface geometry of the surface may be obtained from a three-dimensional pre-operative image of the anatomy, or from geometric mapping and anatomical 3D reconstruction that may be performed by reconstructing an interpolated anatomical surface based on endocardial surface locations that have been visited with a catheter device and a localization system that is suitably registered with the computer-controlled navigation system. Since the three-dimensional data of the surface is available, the unit normal vector $\bar{n}$ at the target location may be determined from this data. The tip of a virtual medical device 24, or the tip of the actual medical device where localization data is available, is positioned against the tissue surface 20 near the target location, and a unit tangent vector (device tip orientation) at the tip of the virtual medical device 24 is defined as $\bar{t}$. The unit vector corresponding to the orientation of the medical device base is defined as $\bar{u}$ shown at 28 in FIG. 1. With the medical device positioned against the surface 20, the field vector of the magnetic navigation system is also defined as $\bar{B}_0$. An orthogonal vector $\bar{a}$ is defined as $\bar{a}'=\bar{t}\times\bar{n}$, and suitably normalized, $$\vec{a} = \frac{\vec{a}'}{|\vec{a}'|}.$$

Next, a vector $\bar{c}$ (indicated at 30) that is orthogonal to unit normal vector $\bar{n}$ is defined as $\bar{c}=\bar{n}\times\bar{a}$, such that $\bar{a}$ a and $\bar{c}$ span the local tangent plane p at point $\bar{x}_0$. Then, two points indicated at 32 and 34 are defined as:

$$\bar{x}_1 = \bar{x}_0 - l\bar{c}, \text{ and}$$

$$\bar{x}_1 = \bar{x}_0 - l\bar{c},$$

where the distance l is approximately 4 to 7 millimeters.

Next, starting from $\bar{x}_1$, incremental steps in the $-\bar{n}$ direction are made (computationally) at an increment of about 1-5 millimeters. The incremental step is made in association with a three-dimensional image model of the surface geometry, which may determine whether the incremental step results in an image threshold crossing. The above distances are suitable for applications of determining the curvature of certain surfaces such as the interior of a heart. It should be noted that the above distances and increments are exemplary in nature, and may be varied for a variety of applications. If an image intensity threshold crossing of the surface occurs during the stepping process (e.g. the intensity value changes from a low value to a high value), the surface is locally positively curved in the device deflection plane. If no intensity threshold crossing of the surface occurs, the surface is locally negatively curved in approximately the device deflection plane. This can be confirmed by incrementally stepping in the $-\bar{n}$ direction starting from $\bar{x}_2$, to confirm the absence of any image threshold crossings at $\bar{x}_2$.

In one preferred embodiment of the present invention, if there is no occurrence of an image intensity threshold crossing, the vector a (defined above) is redefined and set equal to the vector u defining the base of the medical device: $\bar{a}\leftarrow\bar{u}$. In a second preferred embodiment, the vector c is used to redefine a: $a\leftarrow c$. In a third preferred embodiment, the principal directions of curvature of the surface at the target location are determined using the deviation of the shape of a local surface patch away from the local tangent plane as given by standard methods of differential geometry, and the principal direction v corresponding to the minimum signed curvature is used to redefine a: $a\leftarrow v$.

As an illustrative non-limiting example of changing a control variable in order to enhance surface contact, we consider the case of magnetic navigation, where an externally applied magnetic field is used to actuate and generally control the configuration of a magnetically endowed medical device. Other actuation technologies could be used for the same purpose and in these other cases the change of control variable would be mapped suitably as could be determined by persons skilled in the art of the appropriate actuation technology with the help of the teachings contained herein.

In the case of magnetic navigation, in general the external magnetic field can be suitably oriented or rotated to optimize surface contact of the medical device with the local tissue surface. In order to determine the rotation of the medical device, the field vector will be rotated about the (rotation axis) vector $\bar{a}$ (suitably defined in various embodiments as described above) by an angle θ to establish a new field vector defined as:

$$\bar{B}=R_{\bar{a}}(\theta)\bar{B}_0 \quad (1)$$

These methods of the various embodiments generally ensure that the tip of the medical device either directly pushes out against the local tissue surface, or in cases where the surface curvature is not suitably optimal, pushes sideways against the surface in a direction of strongly positive curvature. In either case contact with the local surface position is enhanced and stabilized, which feature is helpful for instance when the tissue surface is in motion, as in the case of the endocardial surface.

If vector $\bar{a}=(a_x,a_y,a_z)$, then a 3×3 skew-symmetric matrix can be defined as:

$$A = \begin{pmatrix} 0 & -a_z & a_y \\ a_z & 0 & -a_x \\ -a_y & a_x & 0 \end{pmatrix} \quad (2)$$

and the rotation matrix for rotating the device about axis $\bar{a}$ can be written as:

$$R_{\bar{a}}(\theta) = I_{3\times 3} + \sin\theta A + (1-\cos\theta)A^2, \quad (3)$$

where I is the 3×3 identity matrix To determine the angle of rotation $\theta$ for the rotation matrix in equation (3), we initially determine the lag angle $\phi = \cos^{-1}(\bar{t} \cdot \bar{B}_0)$. We can use $\theta \sim (\pi/2 - \phi)$ as a reasonable assumption for a good value of $\theta$. The tip of the medical device 24 may then be rotated according to the rotation matrix in equation (3) above. Alternatively, the angle $\theta$ can be defined or set by the user using a slider on a Graphical User Interface. The range of the slider could be limited in some embodiments, so that for example the slider range could correspond to rotation angles $\theta$ in the range (−30 degrees, 45 degrees) in one preferred embodiment. In alternate embodiments different slider ranges could be used. In one preferred embodiment the rotation angle is applied incrementally based on any rotation that has already been applied so that the total rotation angle measured from the original field configuration (corresponding to the catheter tip just touching the target location) is $\theta$ as determined by the slider setting. An example of the latter embodiment is the case when catheter tip localization (position and orientation) information is available. Given the desired angle of rotation that is thus determined, the magnet system is controlled to apply a magnetic field in a direction that provides the requisite over-torque such that catheter tip contact with the tissue surface is enhanced. Once the tip has established firm contact with the surface 20 and is not able to move further, the tip is not aligned with the field vector $\bar{B}_0$. Thus, the lag between the field vector $\bar{B}_0$ and the actual orientation of the tip can provide an indication that the tip of the medical device is in an over-torque contact with the surface 20. Likewise, where an imaging system is used, the prolapse or bend in the distal portion of the medical device 24 that can be seen in the acquired images, or the observation that the device tip has not changed position may also indicate that the tip has established an over-torque contact with the surface 20. The method of determining the rotation of the field vector automatically can also account for the lag angle and other physical properties of the medical device, as given above.

The advantages of the above described embodiment and improvements should be readily apparent to one skilled in the art, as to enabling over-torque of a medical device and thereby enhancing device-tissue contact against a three dimensional surface within a subject body when the device is controlled by a remote navigation system. The actual controls used by the remote navigation system could comprise actuation schemes employing any one or more of magnetic, mechanical, electrostrictive, hydraulic or other actuation means familiar to those skilled in the art. Additional design considerations may be incorporated without departing from the spirit and scope of the invention. Accordingly, it is not intended that the invention be limited by the particular embodiment or form described above, but by the appended claims.

What is claimed is:

1. A method for establishing enhanced contact of a medical device against a three-dimensional surface geometry within a subject body, the method comprising:
    obtaining a target location on a surface within a subject body for a medical device to contact by using an imaging device,
    obtaining local surface geometry information in a neighborhood of the target location, wherein the local surface geometry information includes local surface normal and curvature information determined from at least two points within a local tangent plane containing the target location that are spaced a predetermined distance from the target location, which are used to measure the deviation away from the local tangent plane of a local surface patch;
    using the local surface geometry information to determine a change of at least one control variable for effecting an over-torque of the medical device to enhance contact of the medical device with the target location on the surface; and
    applying the change of the at least one control variable to effect an over-torque and enhance contact of the medical device against the surface.

2. The method of claim 1 wherein the deviation away from the local tangent plane is found by a stepping process that comprises incrementally moving a minimum distance from the at least two points, and determining whether an image intensity threshold, a point where intensity changes from a low value to a high value, has been crossed to determine if the surface is negatively curved or positively curved.

* * * * *